United States Patent [19]
Griffiths et al.

[11] Patent Number: 6,071,490
[45] Date of Patent: Jun. 6, 2000

[54] POSITION EMISSION TOMOGRAPHY USING GALLIUM-68 CHELATES

[75] Inventors: Gary L. Griffiths, Morristown; William J. McBride, Simmit, both of N.J.

[73] Assignee: Immunomedics, Inc., Morris Plains, N.J.

[21] Appl. No.: 09/306,789

[22] Filed: May 7, 1999

Related U.S. Application Data

[60] Provisional application No. 60/084,543, May 7, 1998.

[51] Int. Cl.[7] .......................... A61K 51/00; A61M 36/14
[52] U.S. Cl. ...................... 424/1.49; 424/1.11; 424/1.65; 424/9.4; 424/1.69; 530/330; 530/387.2; 534/10
[58] Field of Search ................................. 424/1.11, 1.65, 424/1.69, 9.1, 9.3, 9.4, 130.1, 141.1; 206/223, 569, 570; 534/7, 10–16; 530/300, 330, 387.1, 387.2

[56] References Cited

U.S. PATENT DOCUMENTS

| | | | |
|---|---|---|---|
| 4,741,900 | 5/1988 | Alvarez et al. | 424/85 |
| 4,867,973 | 9/1989 | Goers et al. | 424/85.91 |
| 5,274,076 | 12/1993 | Barbet et al. | 530/330 |
| 5,686,578 | 11/1997 | Goldenberg | 530/387.3 |
| 5,698,178 | 12/1997 | Goldenberg | 424/1.49 |

FOREIGN PATENT DOCUMENTS

| | | |
|---|---|---|
| 0 173 629 | 3/1986 | European Pat. Off. . |
| 0 419 387 A1 | 3/1991 | European Pat. Off. . |
| 0 623 675 A1 | 11/1994 | European Pat. Off. . |
| WO 96/04313 | 1/1996 | WIPO . |

OTHER PUBLICATIONS

Schuhmacher et al., Multistep Tumor Targeting in Nude Mice . . . , *Cancer Research* 55, 115–123 (1995).
Klivényi et al., Gallium–68 Chelate Imaging . . . , *The Journal of Nuclear Medicine*, vol. 39, No. 10 (1998).
Zöller et al., Establishment and Characterization . . . , *The Journal of Nuclear Medicine*, vol. 33, No. 7, (1992).
Bardiès et al., Bispecific Antibody . . . ,*The Journal of Nuclear Medicine* vol. 37 No. 11 (1996).

*Primary Examiner*—Jose' G. Dees
*Assistant Examiner*—Dameron Jones
*Attorney, Agent, or Firm*—Foley & Lardner

[57] ABSTRACT

A method of delivering Ga-68 to a target site is effected by administering a bi-specific antibody which specifically binds via a primary binding site to a substance produced by or associated with the target site and which specifically binds via a secondary binding site to a subsequently administered chelate-Ga-68 complex, and allowing the antibody to localize at the target site; optionally administering a clearing agent to clear non-localized bi-specific antibody rapidly from circulation; and administering a chelate-Ga-68 complex comprising Ga-68 chelated to Ac-Phe-Lys(DTPA)-Tyr-Lys(DTPA)-NH$_2$ and allowing the chelate-Ga-68 complex to localize at the target site via specific binding by the secondary binding site of the bi-specific antibody. The targeted complex then can be used for PET imaging to give highly resolved images. Alternatively, the Ac-Phe-Lys(DTPA)-Tyr-Lys(DTPA)-NH$_2$ can be conjugated to a targeting antibody fragment and used to elute Ga-68 from a generator, after which it is infused into a patient for direct targeting of the Ga-68 for PET imaging. Reagents and methods of making and using them also are provided.

14 Claims, No Drawings

POSITION EMISSION TOMOGRAPHY USING GALLIUM-68 CHELATES

RELATED APPLICATIONS

This application is based on provisional application Ser. No. 60/084,543 filed May 7, 1998.

BACKGROUND OF THE INVENTION

Positron emission tomography (PET) is a high resolution, non-invasive, imaging technique for the visualization of human disease. In PET, 511 keV gamma photons produced during positron annihilation decay are detected. In the clinical setting, fluorine-18 (F-18) is one of the most widely used positron-emitting nuclides. However, complicated chemical reactions are needed to link F-18 with specific targeting vectors such as antibodies, antibody fragments, recombinant antibody constructs and longer-lived receptor-targeted peptides.

There is a need, therefore, for a method of effecting PET that does not rely on the F-18 isotope.

SUMMARY OF THE INVENTION

It is one object of the present invention to provide a method of effecting PET by delivery of a chelate-Ga-68 complex.

It is another object of the present invention to provide compositions and kits for effecting PET.

In accordance with these and other objects, the present invention provides a method of delivering Ga-68 to a target site comprising: administering a bi-specific antibody which specifically binds via a primary binding site to a substance produced by or associated with the target site and which specifically binds via a secondary binding site to a subsequently administered chelate-Ga-68 complex, and allowing the antibody to localize at the target site;

optionally administering a clearing agent to clear non-localized bi-specific antibody rapidly from circulation, wherein the clearing agent is anti-idiotypic to the primary binding site of the bi-specific antibody; and administering a chelate-Ga-68 complex comprising Ga-68 chelated by Ac-Phe-Lys(DTPA)-Tyr-Lys (DTPA)-NH$_2$ (SEQ ID NO:1) and allowing the chelate-Ga-68 complex to localize at the target site via specific binding by the secondary binding site of the bi-specific antibody.

In another embodiment, the invention provides a method of delivering Ga-68 to a target site comprising: administering a direct targeting agent comprising a targeting species conjugated to a Ga-68 labeled Ac-Phe-Lys(DTPA)-Tyr-Lys (DTPA)-NH$_2$ (SEQ ID NO:1).

DETAILED DESCRIPTION

The present invention provides a method of effecting positron emission tomography (PET) using the radioisotope gallium-68 (Ga-68). Ga-68 has a one-hour half-life and decays with 90% positron abundance with little associated gamma rays. These physical properties make Ga-68 particularly suitable for PET applications.

Ga-68 is obtained from a germanium-68 (Ge-68) generator. Because Ge-68 has a half-life of >240 days, a Ge-68 generator lasts a long time, making Ga-68 economical. The Ga-68 can be eluted from the generator with any chelator for Ga-68, such as DOTA, DTPA or EDTA, according to the method described by Schuhmacher et al., *Int. J. Appl. Radiat. Isot.*, Vol. 32, pages 31–36 (1981). The resulting chelate-Ga-68 complex can be used in the methods discussed below.

In accordance with one embodiment of the present invention, a pretargeting method is used to deliver Ga-68 to a target site. In this method, the in vivo site of interest (i.e., tumor, lesion, focus of infection) is pretargeted with a bi-specific antibody according to the following steps:

(1) a bi-specific antibody is administered which localizes at the target site via specific binding to a substance produced by or associated with the target site, and which specifically binds to a subsequently administered chelate complex;

(2) optionally, a clearing agent is administered to clear non-localized antibody from circulation; and (3) a chelate complex comprising Ga-68 and Ac-Phe-Lys (DTPA)-Tyr-Lys(DTPA)-NH$_2$ (SEQ ID NO:1) is administered and localizes at the target site via specific binding by the bi-specific antibody.

The bi-specific antibody has a primary binding site which specifically binds to a substance produced by or associated with the target site, and localizes at the target site through this specific interaction. The bi-specific antibody also has a secondary binding site which specifically binds to the subsequently administered chelate complex.

The bi-specific antibody comprises at least two antibodies or antibody fragments, or a combination of at least one antibody and at least one antibody fragment. Antibodies contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

The term "monovalent antibody fragment" as used herein denotes Fab' and Fab fragments, normally obtained by cleavage of bivalent fragments or intact immunoglobulin. Fab' antibody fragments are normally and conveniently made by reductive cleavage of F(ab')$_2$ fragments, which themselves are normally made by pepsin digestion of intact immunoglobulin. Fab antibody fragments can be made by papain digestion of intact immunoglobulin, under reducing conditions, or by cleavage of F(ab)$_2$ fragments which result from careful papain digestion of whole Ig. Parham et al., J. Immunol. Methods, 53:133–173, 1982, and Boguslawski et al., J. Immunol. Methods, 120:51–56, 1989, show papain digestion of murine monoclonal IgG$_1$ to F(ab)$_2$. Activation of the papain with thiol, followed by removal of the thiol prior to cleavage, permits cleavage of those immunoglobulins having the papain cleavage site below at least one disulfide bond to occur without further cleavage of the bivalent fragment.

It will be appreciated, however, that monovalent fragments can also include any fragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen binding site and otherwise function in vivo as targeting vehicles in substantially the same way as natural monovalent immunoglobulin fragments.

It will also be understood that the monovalent antibody fragments to be radiolabeled can be fragments which bind to antigens which include but are not limited to antigens produced by or associated with tumors, infectious lesions, microorganisms, parasites, myocardial infarctions, atherosclerotic plaque, or normal organs or tissues.

The antibody fragment-chelate conjugates of the present invention can be prepared by known methods and the methods in, e.g., U.S. Pat. Nos. 5,612,016; 5,637,288; 5,635,603; and U.S. patent application Ser. Nos. 08/456,629; 08/779,556; and 08/456,909. Antibody fragments can be adapted for conjugation to a radioisotope, i.e., Ga-68, for use as a diagnostic imaging agent, herein, for positron emission tomography. This can be achieved by attaching a chelator for a radiometal or paramagnetic ion, according to the present invention, a compound that chelates Ga-68. Such chelators and their modes of attachment to antibodies are well known to the ordinary skilled artisan and are disclosed inter alia in, e.g., Childs et al., J. Nuc. Med., 26:293 (1985); and in Goldenberg U.S. Pat. Nos. 4,331,647, 4,348,376, 4,361,544, 4,468,457, 4,444,744, and 4,624,846. Typical are derivatives of ethylenediamine-tetraacetic acid (EDTA) and diethylenetriaminepentaacetic acid (DPTA). For example, Ac-Phe-Lys(DTPA)-Tyr-Lys(DTPA)-NH$_2$ (SEQ ID NO:1) chelates Ga-68 and can be conjugated to an antibody fragment. These typically have groups on the side chain by which the chelator can be attached to an antibody fragment.

Alternatively, carboxyl or amine groups on a chelator can be activated and then coupled to an antibody fragment by well known methods.

The chelator may be bound to the antibody fragment, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyanate linker disclosed in U.S. Pat. No. 4,680,338.

In accordance with one embodiment, the bi-specific antibody comprises monoclonal antibodies or antibody fragments. In accordance with another embodiment, the bi-specific antibody comprises humanized antibodies or antibody fragments. Monoclonal antibodies (MAb) are usually mouse proteins, and they are not identical to human antibodies. Hence, antibodies from a mouse, when injected into a patient, will eventually be cleared from circulation as being recognized as foreign proteins. Both chains of the antibody molecule can be divided into variable and constant regions. In each antibody, the variable regions differ from one antibody to the next. This is the region that binds the antigen. The constant region of the antibody is the same among antibodies of the same type. The basic structure of a mouse Mab resembles that of a human antibody. However, there are numerous differences between amino acid sequences of the antibodies from the two species. These sequence differences account for the immunogenicity of mouse MAbs in humans. A chimeric Mab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Mab but will be closer to human antibodies in sequence. Chimeric Mabs still contain some mouse sequences, however, and may still be immunogenic. A humanized Mab contains only those mouse amino acids necessary to recognize the antigen. This product is constructed by building into a human antibody framework the amino acids from the mouse complementarity determining regions.

Multispecific, including bispecific and hybrid, antibodies and antibody fragments also may be used for detecting lesions and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today, 5,299 (1984). These antibodies then are linked to an antibody or antibody fragment with chelate specificity to form the targeting antibody.

The antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361, 544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387–398, 1984, showing ready availability.

Additional examples of Mabs generated against infectious organisms that have been described in the literature are noted.

Mabs against the gp120 glycoprotein antigen of human immunodeficiency virus 1 (HIV-1) are known. See, e.g., Rossi et al., Proc. Natl. Acad. Sci. U.S.A., 86:8055–8058, 1990. Other Mabs against viral antigens and viral induced antigens are also known.

Mabs against malaria parasites can be directed against the sporozoite, merozoite, schizont and gametocyte stages. Several groups have developed Mabs to *T. gondii,* the protozoan parasite involved in toxoplasmosis (Kasper et al., J. Immunol. 129:1694–1699, 1982; Id., 130:2407–2412, 1983), and against schistosomular surface antigens (Simpson et al., Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

*Trypanosoma cruzi* is the causative agent of Chagas' disease, and is transmitted by blood-sucking reduviid insects. A Mab has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, other parasites) responsible for the majority of infections in humans, and can be used for in vitro diagnostic purposes. These antibodies, and newer MAbs that can be generated by conventional methods, are appropriate for use in the present invention. The targeting species can be a monoclonal antibody or antibody fragment, and can be humanized, as discussed above.

Antibodies that specifically bind gallium and indium chelates are known, as are methods for incorporating the antibodies or chelate-binding fragments thereof into bispecific targeting conjugates. See, e.g., U.S. Pat. Nos. 5,256,395 and 5,274,076 and Schuhmacher et al., *Cancer Research*, 55:115–123 (1995).

According to the invention, an optional agent can be administered in order to clear non-localized bi-specific antibodies which detach or migrate from the target back into non-target spaces or into the circulatory system. The clearing agent administered can be any known clearing agent.

In one embodiment, a second antibody is administered which is specific to the initially administered bi-specific antibody and clears the non-localized initially administered antibody. The second antibody may be whole IgG or IgM or a fragment of IgG or IgM, so long as it is capable of binding the bi-specific antibody to form a complex which is cleared from circulation and the non-target spaces more rapidly than the bi-specific antibody itself.

In another embodiment a clearing agent comprising a moiety which binds the primary binding site of the primary targeting species (the bi-specific antibody) is administered. That is, the clearing agent binds the region of the primary targeting species (the bi-specific antibody) which binds to the target site. This type of clearing agent may comprise any molecule which is a specific binding complement to the primary binding site of the primary targeting species (the bi-specific antibody). The clearing agents may be non-antibody species that bind to the primary binding site of the targeting antibody. A non-antibody clearing agent may be used which binds to the primary binding site of the primary targeting species (the bi-specific antibody).

In another embodiment of the invention, the clearing agent is anti-idiotypic to the primary binding site of the bi-specific antibody (the site which binds to a substance produced by or associated with the target site), such as an anti-idiotypic antibody. See, for example, U.S. patent application Ser. Nos. 08/486,166 and 08/731,107, the entire contents of which are incorporated by reference. One advantage of this embodiment is that the clearing agent effectively removes non-localized bi-specific antibody from circulation without competitively removing bi-specific antibody already localized at the target site. If the clearing agent is an antibody, it may be humanized, as discussed above with reference to the bi-specific antibody.

The clearing agent also may be modified with sugar residues, such as galactose, in order to enhance clearance. Conjugating the clearing agent to a sugar residue, such as galactose, serves to bind the clearing agent to the hepatic asialoglycoprotein receptor, whereby the clearing agent and clearing agent-primary targeting species complexes are rapidly recognized by liver hepatocytes. Use of galactosylated clearing agents, therefore, ensures near-total hepatocytic recognition and sequestration within minutes post-injection, generally substantially in a single pass through the liver.

The degree of sugar residue modification of the clearing agent determines the blood clearance rate. It is essential that the appropriate degree of modification of the clearing agent for effective clearance with clearing agents for use with this invention. The number of sugar residues per molecule of clearing agent may be determined empirically for each specific clearing agent by routine methods well-known in the art. It is convenient to express the degree of glycosylation in terms of the percentage of lysine residues modified by addition of sugars. For anti-idiotype antibody clearing agents, it has been found that modifying about 22% of the lysine residues does not provide significantly accelerated clearance of non-localized primary targeting conjugate, whereas modifying about 48% of the lysine residues greatly accelerate clearance and modifying about 76% or more of the lysine residues results in virtually total clearance from circulation in a single pass through the liver. This will generally be true for antibody fragments as well, although the percentages may vary somewhat. The degree of glycosylation to achieve substantially complete clearance in one pass is readily determined.

The chelate complex comprises Ga-68 and any chelating agent for Ga-68. For example, diethylenetriamine pentaacetic acid (DTPA), 1,4,7,10-tetraazacyclododecane N, N', N", N'" tetraacetic acid (DOTA), ethylenediamine tetraacetic acid (EDTA) and other known chelators can be used in accordance with the present invention. Ga-68 is readily chelated by these chelating agents. In a preferred embodiment, the chelate complex comprises Ga-68 and a di-DTPA derivative which is Ac-Phe-Lys(DTPA)-Tyr-Lys(DTPA)-NH$_2$ (SEQ ID NO:1).

As discussed above, Ga-68 can be eluted from the generator with a chelating agent. This chelated Ga-68 can be used as the chelate complex in accordance with this method. Because the chelate-Ga-68 complex is relatively small, non-localized complex will clear rapidly through the kidneys.

It may be advantageous to follow labeling with carrier-free Ga-68 from the generator with addition of cold In$^{+3}$ ions or cold Ga$^{+3}$ ions, e.g., as a soluble salt such as the chloride, to saturate the chelator. With certain anti-chelate antibodies, binding to the chelate is improved when it is saturated with metal ions.

The targeting site is a specific site to which the Ga-68 chelate is to be delivered, such as a cell or group of cells, tissue, organ, tumor, or lesion.

Routes of administration for the composition include intravenous, intraarterial, intrapleural, intraperitoneal, intrathecal, subcutaneous or by perfusion. The preferred routes of administration are intravenous and intraarterial. In one embodiment, the composition is administered as a physiological solution of the direct targeting agent comprising a conjugate of a targeting species and chelator which is chelated with Ga-68. In a second embodiment, a physiological solution of the bi-specific antibody is administered, preferably intravenously or intraarterially. A clearing agent in a physiological solution then may be administered, followed by administration of a chelate complex of Ga-68, preferably Ga-68 labeled Ac-Phe-Lys(DTPA)-Tyr-Lys(DTPA)-NH$_2$ (SEQ ID NO:1).

The present invention achieves effective delivery of Ga-68 to the target site in a short time with a high target:non-target ratio of Ga-68. Generally, the chelate also is retained at the target site for several days. This efficient and specific delivery of Ga-68 to the target site enables effective imaging using PET.

In accordance with another embodiment, the invention provides a direct targeting agent comprising Ga-68. The agent comprises a targeting species conjugated to a chelating agent which chelates Ga-68. In a preferred embodiment, the chelating agent which chelates Ga-68 is Ac-Phe-Lys(DTPA)-tyr-Lys(DTPA)NH$_2$ (SEQ ID NO: 1). This agent can be made by eluting Ga-68 from the generator with a conjugate comprising a chelator for Ga-68 and a targeting species.

The targeting species can be an antibody, antibody fragment, or smaller species, e.g., genetically engineered and/or recombinant proteins, and binds a substance produced by or associated with the target site.

A direct targeting agent can be used to deliver Ga-68 to a target site in a single step. In accordance with this method of the present invention, an agent comprising a conjugate of a targeting species, a chelator for Ga-68 and Ga-68 is administered to a patient and allowed to localize at the target site. In a preferred embodiment, the chelator for Ga-68 is the di-DTPA derivative, Ac-Phe-Lys(DTPA)-Tyr-Lys(DTPA)-NH$_2$ (SEQ ID NO:1). If an antibody fragment or smaller targeting species is used, non-localized agent will clear rapidly through the kidneys, and no clearing agent is needed before PET can be effected. Alternatively, if a larger targeting species is used, a clearing agent can be used. This clearing agent may be any known clearing agent, including an anti-idiotypic clearing agent which binds to the binding site of the targeting species, such as those previously discussed.

Like the pretargeting method discussed above, this direct targeting method achieves rapid and efficient delivery of Ga-68 to a target site. With the high target:non-target ratios of Ga-68 achieved by these methods, subsequent PET images will be accurate and reliable.

EXAMPLES

Example 1

Preparation of the Ga-68 Chelate: Ac-Phe-Lys(DTPA)-Tyr-Lys(DTPA)-NH$_2$ (SEQ ID NO:1)

The peptide was assembled by N-α-Fmoc based solid phase peptide synthesis using a 3×30 cm glass column equipped with a coarse glass frit and a three way valve at the base. The resin was mixed using a nitrogen purge through the three way valve up through the glass frit into the resin suspension. The reaction vessel was emptied by switching the three way valve to the waste position and applying nitrogen pressure from the top of the column to force the solvents out through the frit. The Aloc deprotection was carried out according to known procedures.

An Fmoc-Rink amide resin was used to prepare the peptide: Ac-Phe-Lys-(Aloc)-Tyr(But)-Lys(Aloc)-Rink (SEQ ID NO:1) by stepwise coupling of 2.5 eq each of N$^\alpha$-Fmoc-Lys(Aloc)-OH, N$^\alpha$-Fmoc-Tyr(But)-OH, N$^\alpha$-Fmoc-Lys(Aloc)-OH, N$^\alpha$-Fmoc-Phe-OH followed by acetyl capping with 14 eq acetic anhydride. Each coupling cycle consisted of the following: (1) the resin was treated with 40 ml 25% piperidine in DMF for 15 min, (2) washed with 40 mL portions of N-methylpyrrolidinone (NMP) (two times), iso-propanol (IPA) NMP, IPA, NMP (four times).

The Aloc side chain protecting groups were removed from the peptide Ac-Phe-Lys(Aloc)-Tyr(But)-Lys(Aloc)-Rink (SEQ ID NO:1) by mixing 0.41 g of the resin with 8 mL of a solution containing 0.12 g tetrakis(triphenylphosphine) palladium (0), 10 mL DCM, and 1 mL acetic acid. Tributyltin, 1.2 mL was then added and the mixture was vortex mixed for 2 hr at room temperature. The resin was then washed with 8 mL portions of DCM (two times), 2 DIEA in NMP (two times), NMP, IPA, NMP, IPA, NMP (four times) to produce the aloc deprotected peptide: Ac-Phe-Lys-Tyr(But)-Lys-Rink (SEQ ID NO:1).

The DTPA was activated by the following procedure: (4.0 g) was dissolved in 30 mL 1M tetrabutylammonium hydroxide in methanol. The volatile solvent was removed under reduced pressure on a rotary evaporator. The oily residue was then diluted with 100 mL DMF and the volatile solvents were removed under hi-vacuum on the rotary evaporator. The DMF evaporation was repeated two more times then the remaining oil was dissolved in 25 mL of DMF and mixed with 3.9 g HBTU.

The activated DTPA solution (6 mL) was vortex mixed with the deprotected resin (Ac-Phe-Lys-Tyr(But)-Lys-Rink for 24 hr at room temperature. The resin was then washed with 8 mL portions of NMP (two times), IPA, NMP, IPA, NMP (four times) and DCM (two times).

The peptide was cleaved from the resin with 8 mL of a cleavage cocktail consisting of 35 mL TFA, 15 mL DCM, 1 mL anisole, 1 mL ethanedithiol, and 1 mL TIPS. The resin suspension was vortexed at room temperature for 2 hr and the cleavage solution was collected by filtration. the resin was washed with 4 mL more of the fresh cleavage cocktail and the filtrates were combined. The filtrate was then poured into 30 mL diethyl ether and the precipitated crude peptide was collected by centrifugation. The crude precipitate was washed with three 30 mL portions of ether and dried in vacuo. The crude peptide was then purified by preparative HPLC. The fractions were analyzed by HPLC (RT 5.7 min). The fractions which contained the product were combined, and lyophilized to provide the product (21.0 mg, 14%) as a white amorphous solid.

Example 2

PET Imaging of Small Cell Lung Cancer With Pre-Targeting

A patient diagnosed with small cell lung cancer is injected with a bispecific antibody conjugate composed of an Fab' fragment from an anti-small cell lung cancer monoclonal antibody and an Fab' fragment of an anti-DTPA monoclonal antibody. The next day, a 0.5 molar excess of Ga-68-Ac-Phe-Lys(DTPA)-Tyr-Lys(DTPA)-NH$_2$ (SEQ ID NO:1), labeled with an imaging dose of Ga-68 and then saturated with InCl$_3$, is infused intravenously. After 2 hours, 4 hours and 6 hours, PET scans are taken. Well resolved images of tumor in several lobes of the right lung are observed, including small tumors, even after 2 hours.

Example 3

PET Imaging of Colorectal Cancer With Direct Targeting

A solution of a conjugate of an anti-CEA monoclonal antibody Fab' fragment linked through an n-hexyl chain on the antibody hinge region to the phenolic residue of the tyrosine of Ac-Phe-Lys(DTPA)-Tyr-Lys(DTPA)-NH$_2$ (SEQ ID NO:1), in sterile physiological saline is used to elute and chelate an effective imaging dose of Ga-68 from a generator. The conjugate is then infused intravenously into a patient diagnosed with a carcinoma of the tranverse colon. After 2 hours, 4 hours, and 6 hours, PET scans are taken. Well resolved images of the tumor are observed, even after 2 hours.

The preceding examples can be repeated with similar success by substituting the generically or specifically described reactants and/or operating conditions of this invention for those illustrative species exemplified above.

From the foregoing description, one skilled in the art can easily ascertain the essential characteristics of this invention and, without departing from the spirit and scope thereof, can make various changes and modifications of the invention to adapt it to various usages and conditions.

---

What is claimed is:

1. A method of delivering Ga-68 to a target site in a mammal comprising:

administering a bi-specific antibody which specifically binds via a primary binding site to a substance produced by or associated with the target site and which specifically binds via a secondary binding site to a subsequently administered chelate-Ga-68 complex, and allowing the antibody to localize at the target site;

optionally administering a clearing agent to clear non-localized bi-specific antibody rapidly from circulation; and administering a chelate-Ga-68 complex comprising Ga-68 chelated to Ac-Phe-Lys(DTPA)-Tyr-Lys (DTPA)-NH$_2$ (SEQ ID NO:1) and allowing the chelate-Ga-68 complex to localize at the target site via specific binding by the secondary binding site of the bi-specific antibody.

2. The method of claim 1, wherein the bi-specific antibody comprises a monoclonal antibody.

3. The method of claim 1, wherein the bi-specific antibody comprises a monoclonal antibody fragment.

4. The method of claim 1, wherein the bi-specific antibody comprises a humanized antibody.

5. The method of claim 1, wherein the bi-specific antibody comprises a humanized antibody fragment.

6. The method of claim 1, wherein the clearing agent is anti-idiotypic to the primary binding site of the bi-specific antibody.

7. A method of delivering Ga-68 to a target site in a mammal comprising:

administering a direct targeting agent comprising a targeting species conjugated to Ga-68 labeled Ac-Phe-Lys(DTPA)-Tyr-Lys(DTPA)-NH$_2$ (SEQ ID NO:1).

8. A method of preparing a targeting species conjugated to a chelator chelating Ga-68, comprising:

eluting Ga-68 from a Ge-68 generator with a conjugate of a targeting species and Ac-Phe-Lys(DTPA)-Tyr-Lys (DTPA)-NH$_2$ (SEQ ID NO:1).

9. A kit for chelating Ga-68, comprising, in separate containers:

a bi-specific antibody which specifically binds via a primary binding site to a substance produced by or associated with a target site in a mammal and which specifically binds via a secondary binding site to a Ga-68 chelate complex;

optionally a clearing agent that binds the bi-specific antibody;

and Ga-68 labeled Ac-Phe-Lys(DTPA)-Tyr-Lys(DTPA)-NH$_2$ (SEQ ID NO:1), which is specifically bound by the secondary binding site of said bi-specific antibody.

10. The kit of claim 9, wherein the clearing agent is anti-idiotypic to the primary binding site of the bi-specific antibody.

11. A composition for delivering Ga-68 to a target site in a mammal, comprising:

a direct targeting agent comprising a conjugate of a targeting species chelated with Ga-68 labeled Ac-Phe-Lys(DTPA)-Tyr-Lys(DTPA)-NH$_2$ (SEQ ID NO:1), in a pharmaceutically acceptable sterile carrier.

12. A method of positron emission tomography in a mammal, comprising administering a bi-specific antibody or antibody fragment which specifically binds via a primary binding site to a substance produced by or associated with a target site and which specifically binds via a secondary binding site to a subsequently administered Ga-68 chelate complex, and allowing the antibody to localize at the target site; optionally administering a clearing agent to clear non-localized bi-specific antibody or antibody fragment rapidly from circulation; administering a Ga-68 chelate complex comprising Ga-68 chelated to Ac-Phe-Lys(DTPA)-Tyr-Lys (DTPA)-NH$_2$ (SEQ ID NO:1) and allowing the Ga-68 chelate complex to localize at the target site via specific binding by the secondary binding site of the bi-specific antibody or antibody fragment; and detecting sites of accretion of Ga-68 chelate.

13. The method of claim 12, wherein the clearing agent is anti-idiotypic to the primary binding site of the bi-specific antibody or antibody fragment.

14. A method of positron emission tomography in a mammal, comprising administering an antibody fragment-Ga-68-Ac-Phe-Lys(DTPA)-Tyr-Lys(DTPA)-NH$_2$ (SEQ ID NO:1) conjugate, wherein the antibody fragment specifically binds to a substance produced by or associated with a target site, and allowing the chelate conjugate to localize at the target site; and detecting sites of accretion of said conjugate.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: chelating
      agent (DTPA)

<400> SEQUENCE: 1

Phe Lys Tyr Lys